US010597693B2

(12) United States Patent
Orenga et al.

(10) Patent No.: US 10,597,693 B2
(45) Date of Patent: Mar. 24, 2020

(54) ENRICHMENT AND SELECTIVE CULTURE OF MYCOBACTERIA

(71) Applicant: BIOMERIEUX, Marcy l'etoile (FR)

(72) Inventors: Sylvain Orenga, Neuville sur Ain (FR); Audrey Perry, Newcastle Upon Tyne (GB); John Perry, Newcastle Upon Tyne (FR); Clair Preece, Newcastle Upon Tyne (GB)

(73) Assignee: BIOMERIEUX, Marcy l'Etoile (FR)

(*) Notice: Subject to any disclaimer, the term of this patent is extended or adjusted under 35 U.S.C. 154(b) by 73 days.

(21) Appl. No.: 15/549,370

(22) PCT Filed: Feb. 4, 2016

(86) PCT No.: PCT/FR2016/050239
§ 371 (c)(1),
(2) Date: Aug. 7, 2017

(87) PCT Pub. No.: WO2016/124863
PCT Pub. Date: Aug. 11, 2016

(65) Prior Publication Data
US 2018/0030500 A1    Feb. 1, 2018

(30) Foreign Application Priority Data

Feb. 6, 2015  (FR) ...................... 15 50959

(51) Int. Cl.
*C12Q 1/04* (2006.01)
*C12N 1/20* (2006.01)
(52) U.S. Cl.
CPC .............. *C12Q 1/045* (2013.01); *C12N 1/20* (2013.01); *C12Q 1/04* (2013.01); *G01N 2333/35* (2013.01)
(58) Field of Classification Search
CPC . C12Q 1/045; C12Q 1/04; C12N 1/20; G01N 2333/35
See application file for complete search history.

(56) References Cited

U.S. PATENT DOCUMENTS 4,263,398 A      4/1981   Miyashiro et al.
2014/0199724 A1  7/2014   Deol et al.

OTHER PUBLICATIONS

Tam et al. Pharmacodynamics of Polymyxin B against Pseudomonas aeruginosa. Antimicrobial Agents and Chemotherapy, Sep. 2005, p. 3624-3630 (Year: 2005).*
Esther et al. Journal of Clinical Microbiology, vol. 49, 4. pp. 1421-1425, 2011.
Campbell et al. Journal of Clinical Microbiology, vol. 26,1. pp. 1910-1912, 1988.
Laine et al. Journal of Cystic Fibrosis, vol. 8, 2. pp. 143-149, 2009.
Vermis et al. Systemic and Applied Microbiology,vol. 26, 4, pp. 595-600, 2003.
Apr. 26, 2016 Search Report issued in International Patent Application No. PCT/FR2016/050239.
Apr. 26, 2016 Written Opinion issued in International Patent Application No. PCT/FR2016/050239.

* cited by examiner

*Primary Examiner* — Taeyoon Kim
(74) *Attorney, Agent, or Firm* — Oliff PLC

(57) ABSTRACT

A process for the enrichment and selective culture of mycobacteria contained in a biological sample, wherein all or part of the sample is inoculated in/on a culture medium including a nutritive component suitable for the development and growth of mycobacteria, wherein the culture medium includes, as selective agents, at least 9-chloro-9-(4'-diethylamino)phenyl-9,10-dihydro-10-phenylacridine hydrochloride (or C-390) and an agent capable of inhibiting *Pseudomonas aeruginosa* bacteria. The invention also relates to a culture medium suitable for implementing this process for the enrichment and selective culture of mycobacteria.

13 Claims, No Drawings

ENRICHMENT AND SELECTIVE CULTURE OF MYCOBACTERIA

The present invention relates to methods for culturing and isolating mycobacteria. More specifically, it relates to the microbiology methods and the culture media that can be used for the detection, identification, isolation and/or analytical study of mycobacteria, for example those present in biological specimens and samples.

Mycobacteria, which belong to the order Actinomycetales, are thin bacilli which are straight or sometimes slightly curved in shape. Because they have a lipid-rich wall which limits the penetration of dyes, the staining of mycobacteria by conventional techniques and dyes is difficult. However, once stained, the staining of said mycobacteria withstands destaining both with acid and with alcohol. For this reason, they are described as "acid-alcohol-resistant" bacteria.

According to one elementary classification, the various species of mycobacteria are listed according to two major categories.

The first category groups together the strict pathogenic mycobacteria, which parasitize both animals and human beings. These mycobacteria are responsible for tuberculosis (*Mycobacterium tuberculosis*, *Mycobacterium bovis*, *Mycobacterium africanum*, *Mycobacterium microti* and *Mycobacterium canetti*) or for leprosy (*Mycobacterium leprae*).

The second category groups together the saprophytic or commensal mycobacteria, which are usually non-pathogenic. The term then used is "atypical" mycobacteria or "nontuberculous" mycobacteria (NTM). The latter, which are ubiquitous in our environment, are found to be disseminated just about everywhere in soil, plants, dust, water and distribution networks, our food, etc. Generally harmless to human beings, some nontuberculous mycobacteria can, in immunodepressed subjects, cause opportunistic infections which mainly affect the lungs, the skin and the lymphatic system.

Thus, from a clinical point of view but also from a sanitary point of view, whether they are pathogenic or nontuberculous, the detection and/or identification of mycobacteria is of considerable importance. Early and specific detection of these bacteria makes it possible to propose a suitable solution, in terms of therapeutic treatment, of sanitary decontamination, etc. Various techniques exist in this regard, for example gene amplification (by PCR) of specific nucleic sequences, immunodetection of antigens, mass spectrometry, microbiological detection of enzymatic activities, etc.

Whatever they are, these detection/identification methods generally require the culturing of the mycobacteria possibly present in the samples/specimens to be analyzed, in order to obtain an amount suitable for their detection. Whatever they are, these detection/identification methods suffer from the same handicap: the slowness of growth and development of the mycobacteria.

Indeed, compared with other bacteria, with yeasts and with fungi, both pathogenic and saprophytic mycobacteria are characterized by relatively slow growth and development. Moreover, in biological samples in which the presence of mycobacteria is investigated, the mycobacteria are rarely isolated; they are usually contaminated with an accompanying flora, the growth and development of which are much faster. As the cell division cycles progress, the proportion of mycobacteria in the sample decreases, and the difficulty in being able to visualize and identify them is accentuated thereby.

In order to overcome this slowness of growth and development and/or this contamination by other microorganisms, many enrichment culture media and broths which are more or less selective for mycobacteria or for a particular species of mycobacteria have been developed.

Among those most commonly used, the Löwenstein-Jensen medium is a coagulated (non-agar) culture medium comprising a nutritive component based on whole egg, on potato starch, on asparagine, on glycerol and on minerals. This medium also contains malachite green, for the purpose of inhibiting the accompanying flora (more particularly, the Gram-negative bacteria). An addition of penicillin and/or of nalidixic acid has also been proposed in order to increase the selectivity thereof with regard to mycobacteria.

The Coletsos agar medium, of similar composition, additionally contains pyruvate and glutamate, sunflower blue and gelatin.

The Middlebrook 7H9, 7H10 and 7H11 media, which have emerged more recently, are semi-synthetic media which have a nutritive component based on amino acids, fatty acids, pyruvate and mineral salts. These media also contain catalase and bovine albumin (fraction V), which give the mycobacteria protection against various harmful agents (in particular toxic peroxides) possibly present in the biological samples and specimens. The Middlebrook 7H10 medium differs from the Middlebrook 7H9 medium by the presence of malachite green. The Middlebrook 7H11 medium differs from the Middlebrook 7H10 medium in that it is enriched with a pancreatic casein peptone. Many variants to these three Middlebrook media have also been envisioned in order to increase the selectivity thereof with regard to mycobacteria, for example by adding the following selective agents thereto: polymyxin, amphotericin B, nalidixic acid, trimethoprim, azlocillin and vancomycin.

Lastly, the BCSA (for "*Burkholderia cepacia* selective agar") medium, initially developed for culturing and detecting *Burkholderia cepacia*, has been described as being particularly suitable for the development and growth of mycobacteria, more particularly "rapidly growing" mycobacteria (Esther et al.—*Journal of Clinical Microbiology;* 2011, 1421-1425). This is an agar culture medium formulated from a nutritive component comprising casein peptone, sugars (lactose and sucrose), a yeast extract and selective agents such as gentamicin, vancomycin, crystal violet and polymyxin B.

The present invention aims to improve the methods and techniques used for detecting, identifying and/or isolating the mycobacteria present in a biological sample. To do this, the present invention is aimed at improving the enrichment broths and culture media used in these methods and techniques, both in terms of their fertility and in terms of their selectivity with regard to mycobacteria. Likewise, it aims to provide novel compositions of enrichment broth and/or culture medium, capable of allowing the culture and multiplication of mycobacteria, and having improved performance levels in terms of fertility and/or of selectivity with regard to mycobacteria.

Before presenting the invention, the following definitions are given in order to allow better understanding of the invention.

The term "culture medium" is intended to mean a medium comprising all the elements required for the expression of a metabolism and/or for the growth of microorganisms. The culture medium may be solid, semisolid or liquid. The term "solid medium" is intended to mean for example a gelled medium or a coagulated medium. Agar is the conventional gelling agent in microbiology for culturing microorganisms, but it is possible to use gelatin, agarose or other natural or artificial gelling agents.

The term "enrichment broth" denotes more specifically a liquid culture medium.

A culture medium is described as a minimum medium when its composition comprises only the chemical elements strictly required for the growth and multiplication of the microorganisms to be cultured. The following are conventionally found therein:
water (generally distilled or deionized water);
a nutritive component generally comprising:
  a carbon-based source of energy (generally glucose);
  a calcium source (for example $CaCl_2$);
  a nitrogen source (for example $(NH_4)_2SO_4$);
  a sulfur source (for example $(NH_4)_2SO_4$);
  a magnesium source (for example $MgCl_2$);
  an iron source (for example iron citrate);
  a source of trace elements (for example salts of Cu, Zn, Co, Ni, B, Ti);
optionally a pH buffer for maintaining the medium at a suitable pH; and for the solid or semi-solid media, optionally a gelling agent (for example agar, gelatin or agarose).

The addition of particular growth factors and/or of various nutrients makes it possible to reinforce the attributes of the nutritive component and to increase the fertilizing capacity of the medium. The term "enriched" medium is then used. The addition of these growth factors and/or of these nutrients can be carried out by means of chemically defined compounds or compositions, or else by means of complex compositions (for example, fresh blood, sera, yeast extract, whole egg, egg yolk, peptones, etc.).

A culture medium is said to be selective when it comprises at least one selective agent which allows said medium to promote the growth of a target microorganism or of a target group of microorganisms, rather than that of the accompanying flora. These selective agents are essentially compounds with antibiotic and/or antifungal effects, which have a specificity of toxicity (lower toxicity for the target microorganisms than for the accompanying flora).

The term "biological sample" is intended to mean a clinical sample from a specimen of human or animal origin, or a food sample from any type of food. This biological sample may be liquid or solid and mention may be made, in a nonlimiting manner, of a clinical sample of blood, plasma, urine or feces, or of nose, throat, skin, wound, cerebrospinal fluid, bronchoalveolar fluid or expectoration specimens, a food sample from water, from drinks such as milk or fruit juice, from yoghurt, from meat, from eggs, from vegetables, from mayonnaise, from cheese, from fish, etc., a food sample derived from an animal feed, such as in particular a sample derived from animal meals. For the purposes of simplifying the vocabulary, use will be made without distinction of the expressions "biological sample" and "biological specimen".

The present invention thus relates to a process (a method) for the enrichment and selective culture of mycobacteria contained in a biological sample, wherein all or part of said sample is inoculated in/on a culture medium comprising a nutritive component suitable for the development and growth of mycobacteria, characterized in that said culture medium also comprises, as selective agents, at least 9-chloro-9-(4'-diethylamino)phenyl-9,10-dihydro-10-phenylacridine hydrochloride and an agent capable of inhibiting *Pseudomonas aeruginosa* bacteria.

The present invention is based on the general principle of incorporating 9-chloro-9-(4'-diethylamino)phenyl-9,10-dihydro-10-phenylacridine into compositions of culture media envisioned for culturing mycobacteria, in order to increase the selectivity of said media with regard to mycobacteria. This selective agent is also known under the generic name C-390 (CAS 77769-31-4). Up until now essentially used for the purposes of the selective culture of *Pseudomonas aeruginosa* (U.S. Pat. No. 4,263,398 and Campbell et al.—*Journal of Clinical Microbiology;* 1988, 1910-1912) or the isolation of genomovars of the *Burkholderia cepacia* complex (Vermis et al.,—*Systematic and Applied Microbiology;* 2003 (26) 595-600), the inventors have demonstrated that the use of such a compound in the culture media can also result in a good isolation of the mycobacteria and a good elimination of the accompanying flora, in particular of the microorganisms belonging to the genera *Pseudomonas, Enterobacteriaceae, Streptococcus, Burkholderia, Stenotrophomonas, Staphylococcus, Enterococcus, Achromobacter, Acinetobacter, Pandoraea, Bacillus, Elizabethkingia miricola, Haemophilus, Moraxella, Neisseria, Aspergillus, Scedosporium, Candida* and *Geosmithia*.

The inventors have also noted that C-390 also confers on the culture media a slight additional bluish tint which can notably improve the visualization and visual detection of the colonies growing on these media.

Advantageously and according to the invention, the C-390 concentration of the culture medium used to carry out the process for enrichment and selective culture according to the invention is between 2 mg/l and 1000 mg/l, preferably between about 4 mg/l and about 256 mg/l, and even more preferentially between about 8 mg/l and about 128 mg/l.

By way of examples of agents capable of inhibiting *Pseudomonas aeruginosa* bacteria, mention may in particular be made of colistin methanesulfonate, fosfomycin, nalidixic acid, aztreonam, cefsulodine and mangrolide A.

Advantageously and according to the invention, use may also be made, in said culture medium, of an agent capable of inhibiting *Burkholderia cepacia* bacteria, preferentially an agent chosen from fosfomycin, aztreonam and mangrolide A.

According to one preferred embodiment of the invention, said culture medium also comprises at least one additional selective agent chosen from:
  amphotericin B, in particular at a concentration preferentially between 1 mg/l and 200 mg/l, and even more preferentially between 2 mg/l and 50 mg/l;
  nalidixic acid, in particular at a concentration preferentially between 5 mg/l and 200 mg/l, and even more preferentially between 15 mg/l and 100 mg/l;
  vancomycin, in particular at a concentration preferentially between 1 mg/l and 50 mg/l, and even more preferentially between 2 mg/l and 20 mg/l;
  colistin methanesulfonate, in particular at a concentration preferentially between 10 mg/l and 200 mg/l, and even more preferentially between 15 mg/l and 150 mg/l;
  fosfomycin, in particular at a concentration preferentially between 100 mg/l and 3000 mg/l, and even more preferentially between 200 mg/l and 2000 mg/l; and
  malachite green, in particular at a concentration preferentially between 0.05 mg/l and 2 mg/l, and even more preferentially between 0.2 mg/l and 1 mg/l.

According to one preferred mode of the invention, said culture medium comprises, as additional selective agents:
  amphotericin B, at a concentration of between 2 mg/l and 50 mg/l, colistin methanesulfonate, at a concentration of between 15 mg/l and 150 mg/l, fosfomycin, at a concentration of between 200 mg/l and 2000 mg/l.

According to one preferred mode of the invention, in addition to the fosfomycin, said culture medium advantageously comprises glucose-6-phosphate, in particular at a concentration preferentially between 10 mg/l and 50 mg/l.

According to one particular aspect, the present invention is aimed at improving the methods for culturing and/or isolating mycobacteria which are currently in use, by intervening with regard to the composition of the usual culture media (such as Middlebrook media, the Löwenstein-Jensen medium, Columbia medium, BCSA medium) so as to increase the selectivity thereof by inhibiting the non-mycobacteria. To this effect, the present invention proposes to perfect the composition of these culture media by introducing C-390, and optionally other selective agents as previously stated. Likewise, the present invention proposes to improve the fertility thereof through the provision of various nutrients such as: glycerol, a supplement based on oleic acid, on albumin, dextrose and on catalase (or OADC supplement), active carbon, fresh blood, a yeast extract, alpha-ketoglutarate, casein, pyruvate, peptones, amaranth, egg yolk, RNA, polyoxyethylene stearate, or tyloxapol.

In this context, the process for the enrichment and selective culture of mycobacteria according to the invention is advantageously carried out with a culture medium of which the nutritive component reproduces that of a culture medium chosen from:
- a Middlebrook medium (in particular one of the Middlebrook media 7H9, 7H10 and 7H11) optionally supplemented with glycerol and/or an OADC supplement;
- a Löwenstein-Jensen medium;
- a Columbia medium, optionally supplemented with an OADC supplement and/or fresh blood, in particular horse blood; and
- a BCSA medium.

According to one even more preferred mode, the process for the enrichment and selective culture of mycobacteria according to the invention is carried out with a culture medium comprising a nutritive component reproducing that of a Middlebrook medium, supplemented with:
- glycerol, in particular at a concentration preferentially between 2 ml/l and 20 ml/l,
- an OADC supplement, in particular at a concentration preferentially between 50 ml/l and 200 ml/l, and optionally
- one or more nutrients chosen from: fresh blood, a yeast extract, alpha-ketoglutarate, casein, pyruvate, peptones, amaranth, egg yolk, RNA, polyoxyethylene stearate and tyloxapol.

Advantageously and according to the invention, said OADC supplement is an aqueous composition comprising 50 g/l of bovine albumin, 20 g/l of glucose, 0.04 g/l of catalase and 0.5 g/l of oleic acid.

Advantageously and according to this preferred mode of the invention, the process for the enrichment and selective culture of mycobacteria according to the invention is carried out with a culture medium comprising a nutritive component reproducing that of a Middlebrook medium, supplemented with:
- glycerol, in particular at a concentration preferentially between 2 ml/l and 20 ml/l,
- an OADC supplement, in particular at a concentration preferentially between 50 ml/l and 200 ml/l, and
- a yeast extract, in particular at a concentration preferentially between 0.1 g/l and 20 g/l.

Advantageously and according to the invention, said process applies more particularly to the enrichment and to the selective culture of mycobacteria belonging to the species *M. abscessus*, *M. bolletii*, *M. massiliense*, *M. chelonae*, *M. immunogenum*, *M. salmoniphilum*, *M. avium*, *M. tuberculosis*, *M. intracellulare*, *M. malmoense*, *M. gordonae*, *M. kansasii* and *M. fortuitum*.

Advantageously and according to the invention, the colonies of mycobacteria developing on said culture medium are visually pinpointed using chromogenic and/or fluorogenic synthetic substrates specific for enzymatic activities expressed by the mycobacteria being sought. To this effect, mention may be made of 4-methylumbelliferyl-beta-D-glucoside which allows the labeling of the colonies expressing a beta-glucosidase activity.

The present invention also extends to a culture medium suitable for carrying out a process for the enrichment and selective culture of mycobacteria according to the invention. In the case in point, a culture medium according to the invention comprises a nutritive component suitable for the development and growth of mycobacteria, and is characterized in that it also comprises, as selective agents, 9-chloro-9-(4'-diethylamino)phenyl-9,10-dihydro-10-phenylacridine hydrochloride and an agent capable of inhibiting *Pseudomonas aeruginosa* bacteria.

According to one particular embodiment, said culture medium is free of crystal violet.

Advantageously and according to the invention, said culture medium comprises a nutritive component suitable for the development and growth of mycobacteria and, as selective agents, 9-chloro-9-(4'-diethylamino)phenyl-9,10-dihydro-10-phenylacridine hydrochloride and an agent capable of inhibiting *Pseudomonas aeruginosa* bacteria. Said culture medium is also characterized by all or some of the following technical characteristics:
- the C-390 concentration is between 2 mg/l and 1000 mg/l, preferentially between about 4 mg/l and about 256 mg/l, and even more preferentially between about 8 mg/l and about 128 mg/l;
- said culture medium comprises at least one additional selective agent (other than C-390 and the agent chosen for inhibiting *Pseudomonas aeruginosa*), chosen from:
  - amphotericin B, in particular at a concentration preferentially between 1 mg/l and 200 mg/l, and even more preferentially between 2 mg/l and 50 mg/l;
  - nalidixic acid, in particular at a concentration preferentially between 5 mg/l and 200 mg/l, and even more preferentially between 15 mg/l and 100 mg/l;
  - vancomycin, in particular at a concentration preferentially between 1 mg/l and 50 mg/l, and even more preferentially between 2 mg/l and 20 mg/l;
  - colistin methanesulfonate, in particular at a concentration preferentially between 10 mg/l and 200 mg/l, and even more preferentially between 15 mg/l and 150 mg/l; and
  - fosfomycin, in particular at a concentration preferentially between 100 mg/l and 3000 mg/l, even more preferentially between 200 mg/l and 2000 mg/l, and optionally glucose-6-phosphate, in particular at a concentration preferentially between 10 mg/l and 50 mg/l;
- said culture medium comprises, as additional selective agents:
  - amphotericin B, at a concentration of between 2 mg/l and 50 mg/l;
  - colistin methanesulfonate, at a concentration of between 15 mg/l and 150 mg/l;
  - fosfomycin, at a concentration of between 200 mg/l and 2000 mg/l, and glucose-6-phosphate, in particular at a concentration preferentially between 10 mg/l and 50 mg/l;

said culture medium comprises a nutritive component reproducing that of a culture medium chosen from:
a Middlebrook medium, optionally supplemented with glycerol and/or an OADC supplement;
a Löwenstein-Jensen medium;
a Columbia medium, optionally supplemented with an OADC supplement and/or fresh blood, in particular horse blood; and
a BCSA medium;

said culture medium comprises a nutritive component reproducing that of a Middlebrook medium, supplemented with:
glycerol, in particular at a concentration preferentially between 2 ml/l and 20 ml/l,
an OADC supplement, in particular at a concentration preferentially between 50 ml/l and 200 ml/l, and optionally
one or more nutrients chosen from: fresh blood, a yeast extract, alpha-ketoglutarate, casein, pyruvate, peptones, amaranth, egg yolk, RNA, polyoxyethylene stearate and tyloxapol.

Advantageously, the present invention relates to a culture medium comprising a nutritive component consisting of Middlebrook 7H9 medium, supplemented with:
glycerol, at a concentration of between 2 ml/l and 20 ml/l,
an OADC supplement, at a concentration of between 50 ml/l and 200 ml/l, and
a yeast extract, at a concentration of between 0.1 g/l and 20 g/l; and comprising, as selective agents:
C-390, at a concentration of between 2 mg/l and 50 mg/l,
amphotericin B, at a concentration of between 2 mg/l and 50 mg/l,
colistin methanesulfonate, at a concentration of between 15 mg/l and 150 mg/l,
fosfomycin, at a concentration of between 200 mg/l and 2000 mg/l, accompanied by glucose-6-phosphate, at a concentration of between 10 mg/l and 50 mg/l.

According to one advantageous embodiment of the invention, the composition of said culture medium can include one or more markers capable of allowing detection and/or visual identification of the mycobacteria developing in or on said medium. They may in particular be synthetic enzymatic substrates, with chromogenic and/or fluorogenic properties.

The invention also relates to a method, a process for the enrichment and selective culture of mycobacteria, to the use of C-390 for the purposes of culturing and/or isolating mycobacteria, and also to a culture medium, characterized by all or some of the technical characteristics set out above and below.

Other objectives, characteristics and advantages of the invention will emerge in the light of the description which follows and of the examples developed below, the objective of which is to facilitate the understanding of the invention and the use thereof. These examples are given by way of explanation and cannot limit the scope of the invention.

EXAMPLES

Production and Evaluation of Selective Media According to the Invention

1/—Selection of a "Basic" Composition for the Culture of Mycobacteria

Various compositions of culture media, known from the literature as being fertile to mycobacteria, were tested and compared for their capacity to make mycobacteria grow. Some were enriched beforehand. The media tested are the following:

medium A: Middlebrook agar,
medium B: Middlebrook agar enriched with glycerol (4 ml/l),
medium C: Middlebrook agar with Tween 80 (1 g/l),
medium D: Middlebrook agar enriched both with glycerol (4 ml/l) and with an OADC supplement (100 ml/l),
medium E: Middlebrook agar supplemented/enriched both with Tween 80 and with the OADC supplement,
medium F: Columbia agar (oxoid),
medium G: Columbia agar (oxoid), enriched with the OADC supplement,
medium H: Columbia agar with blood,
medium I: BCSA medium (bioMerieux, France).

a) Preparation of Media A to E

The media referenced A to E were prepared from a stock solution consisting of a ten-times concentrated Middlebrook 7H9 culture broth (10× Middlebrook 7H9), having the composition:
ammonium sulfate (5 g/l),
L-glutamic acid (5 g/l),
disodium phosphate (25 g/l),
monopotassium phosphate (10 g/l),
sodium citrate (1 g/l),
magnesium sulfate (0.5 g/l),
calcium chloride (0.005 g/l),
zinc sulfate (0.01 g/l),
copper sulfate (0.01 g/l),
ammonium ferric citrate (0.4 g/l),
pyridoxine (0.01 g/l), and
biotin (0.005 g/l).

The pH of this broth was adjusted to 6.6±0.2. The broth was then sterilized in an autoclave at 116° C. for 10 minutes. It is stored in a refrigerator until used.

To obtain medium A, 50 ml of broth were added to 450 ml of deionized water. 5 g of bacteriological agar are added to the whole mixture to obtain a Middlebrook agar. The whole mixture was then sterilized in an autoclave at 116° C., for 10 minutes.

Media B, C, D and E were prepared similarly to medium A, and contain in addition:
glycerol (4 ml/l) and optionally a supplement based on oleic acid, on albumin, on dextrose and on catalase (OADC supplement; 100 ml/l),
or else:
Tween 80 (1 g/l) and optionally an OADC supplement (100 ml/l).

b) Media F to I

Media F, H and I are commercially available media.

Medium G was prepared similarly to medium F, and contains in addition the OADC supplement (100 ml/l).

c) Evaluation of the Fertility of Media A to I with Regard to the Mycobacteria.

The fertility of each of media A to I was evaluated by means of 20 mycobacterial strains:
12 strains of *Mycobacterium abscessus*,
3 strains of *Mycobacterium bolletii*,
5 strains of *Mycobacterium massiliense*.

These strains, initially stored at −20° C. in glycerol, are thawed and cultured, firstly, on Columbia agar with horse blood (5%). Each strain is then suspended in 1 ml of saline solution (0.85%) until it reaches a turbidity equivalent to the McFarland 0.5 standard (equivalent to approximately 1.5× $10^8$ CFU/ml).

For the mycobacteria which have a tendency to agglutinate, the cells are dispersed with a vortex, in a tube containing 3 glass beads 3 mm in diameter, for 10 minutes.

An aliquot of 1 µl of each suspension of mycobacteria is inoculated onto each of the culture media to be evacuated, and plated out so as to obtain isolated colonies. The cultures are incubated at 30° C. The growth of the colonies is observed for 7 days.

The results obtained are summarized in table 1 below.

TABLE 1

| | Medium A: Middlebrook | Medium B: Middlebrook + glycerol. | Medium C: Middlebrook + Tween 80 | Medium D: Middlebrook + glycerol. + OADC | Medium E: Middlebrook + Tween 80 + OADC |
|---|---|---|---|---|---|
| Number of strains showing growth | 0/20 | 0/20 | 0/20 | 11/20 (55%) | 0/20 |

| | Medium F: Columbia | Medium G: Columbia + OADC | Medium H: Columbia with blood | Medium I: BCSA |
|---|---|---|---|---|
| Number of strains showing growth | 0/20 | 3/20 (15%) | 1/20 (5%) | 6/20 (30%) |

2/—Evaluation of the Effect of Various Nutrients on the Growth of the Mycobacteria On the basis of the formulation of medium D previously tested, the effects of various nutrients on the culture of the mycobacteria were evaluated: active carbon, horse blood, yeast extract, alpha-ketoglutarate, casein, pyruvate, peptones, amaranth, egg yolk emulsion, RNA (Sigma, ref. R6625-25G), polyoxyethylene stearate, tyloxapol.

In a manner very similar to medium D, the following media (denoted J to V) were prepared:
medium J: medium D+active carbon (2 g/l),
medium K: medium D+5% horse blood (50 ml/l),
medium L: medium D+yeast extract (4 g/l),
medium M: medium D+alpha-ketoglutarate (15 g/l),
medium N: medium D+casein (1 g/l),
medium 0: medium D+sodium pyruvate (7 g/l),
medium P: medium D+peptone (10 g/l),
medium K: medium D+amaranth (0.04 g/l),
medium R: medium D+egg yolk emulsion (33 ml/l),
medium S: medium D+RNA (0.05 g/l),
medium T: medium D+polyoxyethylene stearate (0.1 g/l),
medium U: medium D+tyloxapol (5 ml/l),
medium V: medium D+egg yolk emulsion (33 ml/l)+active carbon (4 g/l).

The fertility of these media is evaluated by means of the same 20 mycobacterial strains used in the test previously described, and treated identically before inoculation.

The cultures are incubated at 30° C. The growth of the colonies is monitored for 7 days. Table 2 below summarizes the observations made on the 3rd and 7th days of culture.

3/—Evaluation of the Effect of Various Agents that are Selective with Regard to Mycobacteria On the basis of the formulation of medium L previously developed and tested, the effects of various selective agents were evaluated for their level of selectivity with regard to mycobacteria: amphotericin B (antifungal agent), nalidixic acid, vancomycin, colistin methanesulfonate, C-390 (Biosynth, Switzerland), fosfomycin and malachite green, at various concentrations.

Table 3 below summarizes the results of this evaluation, carried out on the 20 mycobacterial strains used in the tests previously described, and on 95 strains of microorganisms not belonging to the *Mycobacterium* genus, after 7 days of incubation. Among the 95 strains mentioned are:
50 strains of *Pseudomonas aeruginosa,*
10 other strains of non-fermentative bacteria:
1 strain of *Achromobacter xylosoxidans,*
1 strain of *Acinetobacter* sp.,
1 strain of *Burkholderia multivorans,*
1 strain of *Burkholderia cenocepacia,*
1 strain of *Burkholderia cepacia,*
1 strain of *Burkholderia contaminans,*
1 strain of *Pandoraea apista,*
1 strain of *Pandoraea pnomenusa,*
2 strains of *Stenotrophomonas maltophilia,*

TABLE 2

| | Medium D | Medium J: Medium D + carbon | Medium K: Medium D + blood | Medium L: Medium D + yeast extract |
|---|---|---|---|---|
| 3rd day: Number of strains showing growth | 0 | 0 | 13 (65%) | 19 (95%) |
| 7th day: Number of strains showing growth | 11 (55%) | 9 (45%) | 17 (85%) | 20 (100%) |

| Medium M: Medium D + α-ketoglut. | Medium N: Medium D + casein | Medium O: Medium D + pyruvate | Medium P: Medium D + peptone | Medium Q: Medium D + amaranth | Medium R: Medium D + egg yolk |
|---|---|---|---|---|---|
| 0 | 9 (45%) | 3 (15%) | 13 (65%) | 0 | 2 (10%) |
| 14 (70%) | 19 (95%) | 17 (85%) | 19 (95%) | 17 (85%) | 19 (95%) |

| Medium S: Medium D + RNA | Medium T: Medium D + polyoxy. st. | Medium U: Medium D + tyloxapol | Medium V: Medium D + egg yolk + carbon |
|---|---|---|---|
| 1 (5%) | 1 (5%) | 0 | 0 |
| 17 (85%) | 18 (90%) | 15 (75%) | 18 (90%) |

7 strains of enterobacteria:
  1 strain of *Escherichia coli*,
  1 strain of *Klebsiella pneumoniae*,
  1 strain of *Providentia rettgeri*,
  1 strain of *Enterobacter cloacae*,
  1 strain of *Enterobacter aerogenes*,
  1 strain of *Serratia marcescens*,
  1 strain of *Citrobacter freundii*,
10 strains of species of Gram-positive bacteria:
  2 strains of *Staphylococcus aureus*,
  1 strain of *Staphylococcus epidermidis*,
  1 strain of *Streptococcus pyogenes*,
  1 strain of *Streptococcus pneumoniae*,
  1 strain of *Streptococcus salivarius*,
  1 strain of *Streptococcus gordonii*,
  1 strain of *Enterococcus faecium*,
  1 strain of *Enterococcus faecalis*, and
  1 strain of *Bacillus subtilis*.
8 strains of fungi/yeasts:
  1 strain of *Candida albicans*,
  1 strain of *Candida glabrata*,
  2 strains of *Aspergillus fumigatus*,
  1 strain of *Aspergillus terreus*,
  1 strain of *Scedosporium apiospermum*,
  1 strain of *Scedosporium prolificans*,
  1 strain of *Rasamsonia (Geosmithia) argillacea*.

In this table 3, the results are presented as number and as percentage of strains having shown growth on the medium in question after 7 days of culture. The notations NS and NT mean respectively "not significant" (inhibition of bacteria by amphotericin B) and "not tested" (action of the antibacterial agents on the yeasts and fungi).

TABLE 3

|  | Medium L | Medium L + amphotericin B | | | Medium L + nalidixic acid | | |
| --- | --- | --- | --- | --- | --- | --- | --- |
|  |  | 5 mg/l | 10 mg/l | 20 mg/l | 16 mg/l | 32 mg/l | 64 mg/l |
| Mycobacteria | 20 (100%) | 20 (100%) | 20 (100%) | 20 (100%) | 20 (100%) | 20 (100%) | 20 (100%) |
| *Pseudomonas aeruginosa* | 50 (100%) | NS | NS | NS | 50 (100%) | 43 (86%) | 35 (70%) |
| Other non-fermentative bacteria | 10 (100%) | NS | NS | NS | 10 (100%) | 10 (100%) | 10 (100%) |
| Enterobacteria | 7 (100%) | NS | NS | NS | 4 (57%) | 0 | 0 |
| Gram-positive bacteria | 10 (100%) | NS | NS | NS | 9 (90%) | 8 (80%) | 7 (70%) |
| Fungi/yeasts | 8 (100%) | 6 (75%) | 4 (50%) | 3 (37.5%) | NT | NT | NT |

|  | Medium L + vancomycin | | | Medium L + colistin methanesulfonate | | | Medium L + C-390 | | |
| --- | --- | --- | --- | --- | --- | --- | --- | --- | --- |
|  | 2.5 mg/l | 5.0 mg/l | 10 mg/l | 32 mg/l | 64 mg/l | 128 mg/l | 32 mg/l | 64 mg/l | 128 mg/l |
| Mycobacteria | 19 (95%) | 19 (95%) | 19 (95%) | 20 (100%) | 20 (100%) | 20 (100%) | 19 (95%) | 19 (95%) | 19 (95%) |
| *Pseudomonas aeruginosa* | 50 (100%) | 50 (100%) | 50 (100%) | 5 (10%) | 5 (10%) | 5 (10%) | 46 (92%) | 45 (90%) | 35 (70%) |
| Other non-fermentative bacteria | 9 (90%) | 9 (90%) | 9 (90%) | 10 (100%) | 10 (100%) | 10 (100%) | 7 (70%) | 4 (40%) | 2 (20%) |
| Enterobacteria | 7 (100%) | 7 (100%) | 7 (100%) | 3 (43%) | 3 (43%) | 3 (43%) | 0 | 0 | 0 |
| Gram-positive bacteria | 0 | 0 | 0 | 7 (70%) | 6 (60%) | 5 (50%) | 0 | 0 | 0 |
| Fungi/yeasts | NT | NT | NT | NT | NT | NT | NT | NT | NT |

|  | Medium L + fosfomycin | | | Medium L + malachite green | | |
| --- | --- | --- | --- | --- | --- | --- |
|  | 400 mg/l | 800 mg/l | 1600 mg/l | 0.125 mg/l | 0.25 mg/l | 0.5 mg/l |
| Mycobacteria | 20 (100%) | 20 (100%) | 20 (100%) | 16 (80%) | 20 (100%) | 20 (100%) |
| *Pseudomonas aeruginosa* | 15 (30%) | 8 (16%) | 6 (12%) | 50 (100%) | 50 (100%) | 50 (100%) |
| Other non-fermentative bacteria | 6 (60%) | 6 (60%) | 5 (50%) | 10 (100%) | 10 (100%) | 10 (100%) |
| Enterobacteria | 3 (43%) | 2 (29%) | 2 (29%) | 7 (100%) | 7 (100%) | 7 (100%) |
| Gram-positive bacteria | 0 | 0 | 0 | 10 (100%) | 10 (100%) | 9 (90%) |
| Fungi/yeasts | NT | NT | NT | NT | NT | NT |

4/—Optimization of the Media Selective for Mycobacteria According to the Invention In the light of the previous data, two further selective culture media, denoted medium W and medium X, were developed. These media were developed from the composition of medium L, which is an enriched culture medium as previously described, to which a particular combination of selective agents was added. The composition of said selective media is summarized as follows:

medium W: medium L +
  colistin methanesulfonate(32 mg/l) + fosfomycin(400 mg/l) +
    glucose-6-phosphate (25 mg/l) + amphotericin B(5 mg/l)

medium X: medium L + colistin methanesulfonate(32 mg/l) +
    fosfomycin(400 mg/l) + glucose-6-phosphate (25 mg/l) +
      amphotericin B (5 mg/l) + C-390 (32 mg/l).

These two media were tested on 188 strains of microorganisms:
98 strains of nontuberculous mycobacteria:
  52 strains of *Mycobacterium abscessus*,
  3 strains of *Mycobacterium bolletii*,
  34 strains of *Mycobacterium chelonae*,
  1 strain of *Mycobacterium immunogenum*,
  6 strains of *Mycobacterium massiliense*,
  2 strains of *Mycobacterium salmoniphilum*,
94 strains of microorganisms not belonging to the *Mycobacterium* genus:
  54 strains of *Pseudomonas aeruginosa*,
  15 other strains of non-fermentative bacteria:
    1 strain of *Achromobacter* sp1,
    1 strain of *Achromobacter xylosoxidans*,
    1 strain of *Acinetobacter* sp.,
    1 strain of *Acinetobacter baumannii*,
    1 strain of *Burkholderia cepacia*,
    1 strain of *Burkholderia contaminans*,
    1 strain of *Burkholderia multivorans*,
    1 strain of *Burkholderia stabilis*,
    1 strain of *Elizabethkingia miricola*,
    1 strain of *Pandoraea apista*,
    1 strain of *Pandoraea pnomenusa*,
    4 strains of *Stenotrophomonas maltophilia*,
  7 strains of enterobacteria (the same as those previously mentioned),
  10 strains of Gram-positive bacteria (the same as those previously mentioned),
  8 strains of fungi/yeasts (the same as those previously mentioned).

In this table 4, the results are presented as number and as percentage of strains having shown growth on the medium in question and after 7 days of culture.

TABLE 4

|  | Medium L | Medium W: Medium L + colistin methanesulfonate (32 mg/l) + fosfomycin (400 mg/l) + G6P (25 mg/l) + Amp B (5 mg/l) | Medium X: Medium L + colistin methanesulfonate (32 mg/l) + fosfomycin (400 mg/l) + G6P (25 mg/l) + Amp B (5 mg/l) + C-390 (32 mg/l) |
|---|---|---|---|
| *M. abscessus* (52) | 52 | 52 | 51 |
| *M. boletti* (3) | 3 | 3 | 3 |
| *M. chelonae* (34) | 34 | 34 | 34 |
| *M. immonogenum* (1) | 1 | 1 | 1 |
| *M. massiliense* (6) | 6 | 6 | 6 |
| *M. salmoniphilum* (2) | 2 | 2 | 2 |
| Total mycobacteria (98): | 98 (100%) | 98 (100%) | 97 (99%) |
| *P. aeruginosa* (54) | 54 | 0 | 0 |
| Other non-fermentative bacteria (15) | 14 | 9 | 6 |
| Enterobacteria (7) | 7 | 2 | 0 |
| Gram-positive bacteria (10) | 10 | 0 | 0 |
| Fungi/yeasts (8) | 8 | 3 | 0 |
| Total non-mycobacteria (94): | 93 (99%) | 14 (15%) | 6 (6%) |

5/—Validation of the Composition of Medium X for the Culture and Selection of *Mycobacterium tuberculosis*

On the basis of the composition of medium X above, a liquid selective culture medium was formulated. This liquid medium X (without agar) was tested for the detection of mycobacteria, in particular of *Mycobacterium tuberculosis*, in the context of an analysis of sputum samples originating from 32 patients not suffering from cystic fibrosis and from 56 patients suffering from cystic fibrosis.

To do this, the BacT/ALERT® 3D automated microbial detection system (bioMerieux, France) was used. Flasks containing the liquid medium X (or broth X) were incubated in the automated detection device for at least 28 days, and compared with the BacT/ALERT® MP reagent conventionally recommended for the detection of mycobacteria.

The composition of this reagent corresponds schematically to a Middlebrook 7H9 medium supplemented with oleic acid, glycerol, bovine serum albumin, amaranth and a cocktail of antibiotics (amphotericin B, azlocillin, nalidixic acid, polymyxin B, trimethoprim and vancomycin).

By examination under a microscope and staining with auramine, the presence of acid-alcohol-resistant bacilli was demonstrated in the 32 sputum samples collected from the patients not suffering from cystic fibrosis. Prior to their inoculation in BacT/ALERT® flasks, containing either the BacT/ALERT® MP broth or broth X, these 32 samples were treated with sodium hydroxide in order to remove the non-mycobacterial species present in the samples, or at least to reduce the viability thereof, in accordance with the standard British methods. 64 BacT/ALERT® flasks were thus prepared and then incubated at 35° C. in a BacT/ALERT® automated device.

As regards the 56 samples collected from the patients suffering from cystic fibrosis, they were subjected to two distinct decontamination protocols, a treatment with acid and a treatment with sodium hydroxide, in accordance with the standard British methods, before their inoculation in the BacT/ALERT® flasks. 224 flasks were thus prepared:
- 56 flasks containing the BacT/ALERT® MP broth, in which a sample pretreated with acid is inoculated,
- 56 flasks containing the BacT/ALERT® MP broth, in which a sample pretreated with sodium hydroxide is inoculated,
- 56 flasks containing broth X, in which a sample pretreated with acid is inoculated,
- 56 flasks containing broth X, in which a sample pretreated with sodium hydroxide is inoculated.

Results of these various cultures are summarized in tables 5, 6 and 7 below.

Tables 5 and 6 teach information on the nature of the mycobacteria identified in the samples (collected respectively from the patients not suffering from cystic fibrosis and from the patients suffering from cystic fibrosis), and the number of flasks in which they were detected.

Table 7 presents the average detection times (in days) for each of the species of mycobacteria detected and identified, as a function of the culture medium used.

TABLE 5

|  | Samples from patients not suffering from cystic fibrosis | | |
| --- | --- | --- | --- |
|  | Broth X | BacT/ALERT ® MP | Combined results |
| M. tuberculosis | 18 | 18 | 18 |
| M. avium | 9 | 9 | 10 |
| M. intrcellulare | 2 | 2 | 2 |
| M. malmoense | 2 | 2 | 2 |
| Total number of strains | 31 | 31 | 32 |
| Sensitivity | 97% | 97% |  |
| Number of flasks contaminated with a non-mycobacterial flora | 0 | 0 | 0 |

TABLE 6

|  | Samples from patients suffering from cystic fibrosis | | |
| --- | --- | --- | --- |
|  | Broth X | BacT/ALERT ® MP | Combined results |
| M. abscessus | 6 | 3 | 6 |
| M. avium | 1 | 0 | 1 |
| Total number of strains | 7 | 3 | 7 |
| Sensitivity | 100% | 43% |  |
| Number of flasks contaminated with a non-mycobacterial flora | 7/112 (6.25%) | 33/112 (29.5%) |  |

TABLE 7

|  | Broth X | BacT/ALERT ® MP |
| --- | --- | --- |
| M. tuberculosis | 14.8 | 10.8 |
| M. avium | 13.1 | 10.8 |
| M. intracellulare | 7.9 | 6.2 |
| M. malmoense | 18.6 | 15.7 |
| M. abscessus | 4.2 | 5 |

In total, 39 mycobacterial isolates were recovered from the 88 initial specimens. 34 isolates were recovered by means of the BacT/ALERT® MP "standard" reagent flasks (i.e. a sensitivity of 87%), compared with 38 with the flasks of broth X according to the invention (i.e. a sensitivity of 97%). These data show that the selective medium proposed by the present invention is relatively efficient for the culture, enrichment and isolation of mycobacteria.

6/—Preparation and Validation of a Selective Medium According to the Invention, Medium Y a) Composition and Preparation of Medium Y The composition of medium Y is the following (for approximately 1600 ml of composition):
- potato starch (30 g),
- asparagine (3.6 g),
- monopotassium phosphate (2.4 g),
- magnesium citrate (0.6 g),
- magnesium sulfate (0.24 g),
- whole egg homogenate (1 l),
- glycerol (12 ml), and
- C-390 (51.2 mg).

This composition corresponds to that of a Löwenstein-Jensen medium, to which C-390 is added, so as to obtain a final concentration of 32 mg/l. Medium Y is prepared therefrom, according to a process identical to that of a Löwenstein-Jensen medium (cf. *Handbook of Microbiological Media*, Ronald M. Atlas, 4th edition, 2010).

b) Summary Evaluation of the Fertility and Selectivity of Medium Y with Regard to the Mycobacteria Medium Y, formulated in inclined tubes, was tested for the culture of various bacterial strains:
- 1 strain of *Mycobacterium fortuitum* (inoculum calibrated at 0.5 McFarland and diluted to 1/10 000),
- 4 strains of *Staphylococcus aureus* (inocula calibrated at 0.5 McFarland and diluted to 1/100), and
- 3 strains of *Pseudomonas aeruginosa* (inocula calibrated at 0.5 McFarland and diluted to 1/100).

The growth of these strains, incubated at 37° C., was followed day by day. The results obtained, presented as percentages of coverage of the slope, are compiled in table 8 below.

The results of these first tests agree relatively well with the results noted with medium X, formulated on the basis of a Middlebrook composition, namely: good growth of the mycobacterial strain, total inhibition of the *S. aureus* strains, and partial inhibition with differential selectivity with regard to the *P. aeruginosa* strains.

TABLE 8

|  | Growth (% coverage of the slope) | | | | | |
| --- | --- | --- | --- | --- | --- | --- |
|  | Day 1 | Day 4 | Day 5 | Day 6 | Day 7 | Day 8 |
| M. fortuitum (ATCC 6841-4) | 0 | 60 | 80 | 80 | 80 | 80 |
| S. aureus (ATCC 25923) | 0 | 0 | 0 | 0 | 0 | 0 |
| S. aureus (ATCC 43300) | 0 | 0 | 0 | 0 | 0 | 0 |
| S. aureus (NCTC 12493) | 0 | 0 | 0 | 0 | 0 | 0 |
| S. aureus (11 08 078) | 0 | 0 | 0 | 0 | 0 | 0 |
| P. aeruginosa (ATCC 27853) | 98 | 98 | 98 | 98 | 98 | 98 |

TABLE 8-continued

| | Growth (% coverage of the slope) | | | | | |
|---|---|---|---|---|---|---|
| | Day 1 | Day 4 | Day 5 | Day 6 | Day 7 | Day 8 |
| P. aeruginosa (08 06 075) | 0 | 2 | 2 | 2 | 5 | 20 |
| P. aeruginosa (08 06 058) | — | — | 25 | 25 | 25 | 25 |

Medium Y, formulated in inclined tubes, was also tested for the culture of slowly growing mycobacterial strains:
1 strain of *Mycobacterium tuberculosis*,
1 strain of *Mycobacterium bovis*, and
1 strain of *Mycobacterium gordonae*.

These tests were carried out with inocula calibrated at 0.5 McFarland and diluted to 1/10 000.

The results obtained, presented as percentages of coverage of the slope, are compiled in table 9 below, and compared to those of a culture on the Löwenstein-Jensen medium.

TABLE 9

| | Growth (% coverage of the slope) | | | | | |
|---|---|---|---|---|---|---|
| | M. tuberculosis (ATCC 25177) | | M. bovis (14-510617-01) | | M. gordonae (14-233192-01) | |
| | Löw.-Jen. | Medium Y | Löw.-Jen. | Medium Y | Löw.-Jen. | Medium Y |
| Day 7 | 5 | 5 | 0 | 0 | 0 | 0 |
| Day 12 | 30 | 10 | 0 | 0 | 5 | 0 |
| Day 19 | 50 | 50 | 5 | 5 | 60 | 80 |

TABLE 9-continued

| | Growth (% coverage of the slope) | | | | | |
|---|---|---|---|---|---|---|
| | M. tuberculosis (ATCC 25177) | | M. bovis (14-510617-01) | | M. gordonae (14-233192-01) | |
| | Löw.-Jen. | Medium Y | Löw.-Jen. | Medium Y | Löw.-Jen. | Medium Y |
| Day 26 | 55 | 70 | 10 | 20 | 60 | 80 |
| Day 40 | 60 | 80 | 50 | 95 | 70 | 80 |

7/—Supplementary Data: Sensitivity of Various Bacteria and of Various Fungal Species with Regard to C-390

An evaluation of the sensitivity to C-390 of various microorganisms capable of infecting the airways was carried out. This evaluation was carried out using medium W of example 4, containing a variable concentration of C-390. Table 10 below collates the observations collected with regard to the intensity of growth of the strains tested as a function of the C-390 concentration of the medium. The abbreviations NG ("no growth") and Tr ("traces") signify that no growth was observed or only a few not very significant traces.

TABLE 10

| | C-390 (mg/l) | | | | | | | |
|---|---|---|---|---|---|---|---|---|
| Strains | 0 | 0.5 | 1 | 2 | 4 | 8 | 16 | 32 |
| *Burkholderia ambifaria* (LMG 19467) | + | NG | NG | NG | NG | NG | NG | NG |
| *Burkholderia anthina* (20983) | + | + | Tr | NG | NG | NG | NG | NG |
| *Burkholderia cenocepacia* (640328) | + | + | + | + | + | + | NG | NG |
| *Burkholderia cenocepacia* (672834P) | + | + | + | + | +/− | NG | NG | NG |
| *Burkholderia cenocepacia* (LMG 18832) | + | ++ | ++ | ++ | + | NG | NG | NG |
| *Burkholderia cenocepacia* (LMG 18830) | + | + | + | + | + | + | +/− | NG |
| *Burkholderia cepacia* (LMG 18821) | + | + | + | + | + | + | NG | NG |
| *Burkholderia cepacia* (LMG 1222) | + | + | + | Tr | NG | NG | NG | NG |
| *Burkholderia contaminans* (40007X) | + | + | + | Tr | NG | NG | NG | NG |
| *Burkholderia dolosa* (LMG21820) | + | + | Tr | NG | NG | NG | NG | NG |
| *Burkholderia gladioli* (ENV) | + | + | ++ | ++ | ++ | + | NG | NG |
| *Burkholderia multivorans* (645914C) | + | + | +/− | NG | NG | NG | NG | NG |
| *Burkholderia multivorans* (672832Y) | + | + | + | + | Tr | NG | NG | NG |
| *Burkholderia multivorans* (LMG 18824) | ++ | + | ++ | ++ | NG | NG | NG | NG |
| *Burkholderia multivorans* (LMG 18822) | ++ | ++ | ++ | + | NG | NG | NG | NG |
| *Burkholderia pyrrocinia* (LMG 21824) | ++ | ++ | ++ | ++ | NG | NG | NG | NG |
| *Burkholderia stabilis* (716237) | + | + | + | + | Tr | Tr | NG | NG |
| *Burkholderia stabilis* (LMG18870) | + | + | +/− | NG | NG | NG | NG | NG |
| *Burkholderia vietnamiensis* (744978N) | + | + | Tr | NG | NG | NG | NG | NG |
| *Burkholderia vietnamiensis* (LMG 18835) | ++ | + | NG | NG | NG | NG | NG | NG |
| *Aspergillus fumigatus* (Anon) | ++ | Tr | NG | NG | NG | NG | NG | NG |
| *Aspergillus terreus* (Anon) | ++ | + | NG | NG | NG | NG | NG | NG |
| *Scedosporium apiospermum* (Anon) | ++ | + | + | NG | NG | NG | NG | NG |
| *Scedosporium prolificans* (Anon) | ++ | NG | NG | NG | NG | NG | NG | NG |
| *Geosmithia argillacea* (Anon) | + | NG | NG | NG | NG | NG | NG | NG |
| *Fusarium oxysporum* (ENV) | ++ | ++ | + | + | + | NG | NG | NG |
| *Aspergillus flavus* (ENV) | ++ | ++ | ++ | ++ | + | NG | NG | NG |

The invention claimed is:

1. A process for the enrichment and selective culture of mycobacteria contained in a biological sample, the process comprising:
    inoculating all or part of the biological sample in/on a culture medium comprising:
        a nutritive composition reproducing that of a Middlebrook medium supplemented with at least:
        glycerol,
        a supplement based on oleic acid, albumin, dextrose, and catalase (an OADC supplement), and
        a yeast extract;
            9-chloro-9-(4'-diethylamino)phenyl-9,10-dihydro-10-phenylacridine hydrochloride (C-390); and
            an agent capable of inhibiting *Pseudomonas aeruginosa* bacteria.

2. The process as claimed in claim 1, wherein the C-390 concentration of the culture medium is between 2 mg/l and 1000 mg/l.

3. The process as claimed in claim 1, wherein the agent capable of inhibiting *Pseudomonas aeruginosa* bacteria is chosen from: colistin methanesulfonate, fosfomycin, nalidixic acid, aztreonam, cefsulodine and mangrolide A.

4. The process as claimed in claim 1, wherein the culture medium also comprises an agent capable of inhibiting *Burkholderia cepacia* bacteria.

5. The process as claimed in claim 1, wherein the culture medium also comprises at least one selective agent chosen from: amphotericin B, nalidixic acid, vancomycin, colistin methanesulfonate, fosfomycin and malachite green.

6. The process as claimed in claim 5, wherein the culture medium comprises, at least one selective agent chosen from:
    amphotericin B, at a concentration of between 2 mg/l and 50 mg/l;
    colistin methanesulfonate, at a concentration of between 15 mg/l and 150 mg/l; and
    fosfomycin, at a concentration of between 200 mg/l and 2000 mg/l.

7. The process as claimed in claim 6, wherein the culture medium also comprises, in addition to the fosfomycin, glucose-6-phosphate, at a concentration of between 10 mg/l and 50 mg/l.

8. A process for the enrichment and selective culture of mycobacteria contained in a biological sample, the process comprising:
    inoculating all or part of the biological sample in/on a culture medium comprising:
        a nutritive composition reproducing that of a Middlebrook medium, supplemented with:
        glycerol, at a concentration of between 2 ml/l and 20 ml/l,
        an OADC supplement, at a concentration of between 50 ml/l and 200 ml/l, and
        a yeast extract, at a concentration of between 0.1 g/l and 20 g/l;
            9-chloro-9-(4'-diethylamino)phenyl-9,10-dihydro-10-phenylacridine hydrochloride (C-390); and
            an agent capable of inhibiting *Pseudomonas aeruginosa* bacteria.

9. A process for the enrichment and selective culture of mycobacteria contained in a biological sample, the process comprising:
    inoculating all or part of the biological sample in/on a culture medium comprising:
        a nutritive composition reproducing that of a Löwenstein-Jensen medium;
        C-390; and
        an agent capable of inhibiting *Pseudomonas aeruginosa* bacteria.

10. The process as claimed in claim 9, wherein the C-390 concentration of the culture medium is between 2 mg/l and 1000 mg/l.

11. The process as claimed in claim 9, wherein the agent capable of inhibiting *Pseudomonas aeruginosa* bacteria is chosen from: colistin methanesulfonate, fosfomycin, nalidixic acid, aztreonam, cefsulodine and mangrolide A.

12. The process as claimed in claim 9, wherein the culture medium also comprises an agent capable of inhibiting *Burkholderia cepacia* bacteria.

13. The process as claimed in claim 9, wherein the culture medium also comprises at least one selective agent chosen from: amphotericin B, nalidixic acid, vancomycin, colistin methanesulfonate, fosfomycin and malachite green.

* * * * *